(12) United States Patent
Mao et al.

(10) Patent No.: US 7,056,719 B2
(45) Date of Patent: Jun. 6, 2006

(54) POLYPEPTIDE-PHOSPHATIDIC ACID PHOSPHATASE 29.81 AND THE POLYNUCLEOTIDE ENCODING SAID POLYPEPTIDE

(75) Inventors: Yumin Mao, Shanghai (CN); Yi Xie, Shanghai (CN)

(73) Assignee: Shanghai Bio Window Gene Development, Inc., Shanghai (CN)

( * ) Notice: Subject to any disclaimer, the term of this patent is extended or adjusted under 35 U.S.C. 154(b) by 460 days.

(21) Appl. No.: 10/362,239

(22) PCT Filed: Aug. 20, 2001

(86) PCT No.: PCT/CN01/01253

§ 371 (c)(1),
(2), (4) Date: Feb. 21, 2003

(87) PCT Pub. No.: WO02/26798

PCT Pub. Date: Apr. 4, 2002

(65) Prior Publication Data

US 2004/0096841 A1    May 20, 2004

(30) Foreign Application Priority Data

Aug. 23, 2000 (CN) .............................. 00 1 19718

(51) Int. Cl.
*C12N 9/12* (2006.01)
*C12N 15/63* (2006.01)
*C12N 15/54* (2006.01)
*C12N 15/79* (2006.01)

(52) U.S. Cl. ................ 435/196; 435/252.3; 435/320.1; 536/23.2

(58) Field of Classification Search ................ 435/196, 435/252.3, 320.1; 536/23.1, 23.2
See application file for complete search history.

(56) References Cited

FOREIGN PATENT DOCUMENTS

| WO | 98/46730 | 10/1998 |
|----|----------|---------|
| WO | 00/05385 | 2/2000  |

OTHER PUBLICATIONS

Sequence alignment between Accession No. ABA08421 & SEQ ID No.: 1 [WO200157188].*

* cited by examiner

*Primary Examiner*—Tekchand Saidha
(74) *Attorney, Agent, or Firm*—Crowell & Moring LLP

(57) ABSTRACT

The invention disclosed a new kind of polypeptide-phosphatidic acid phosphatase 29.81 and the polynucleotide encoding said polypeptide and a process for priducing the polypeptide by DNA recombinant methods. It also disclosed the method of applying the polypeptide for the treatment of various kinds of diseases, such as peripheral nervous demyelination, night blindness, rachitis, fatty liver, bronchial asthma and peptic ulcer. The antagonist of the polypeptide and therapeutic use of the same is also disclosed. In addition, it refers to the use of polynucleotide encoding said phosphatidic acid phosphatase 29.81.

6 Claims, 1 Drawing Sheet

Identity = 79/218 (36%), Similarity = 125/218 (57%)

```
Query:    10  VRALLFGVFVFTEFLDPFQRVIQPEEIWLYKNPLVQSDNIPTRLMFAISFLTPLAVICVV  69
              +  +L + +    + PF R+  + +    K P  + + +P   +   + L P+ ++ V
Sbjct:    28  ILVILIAIEIGLNLISPFYRYVGKDMMTDLKYPF-KDNTVPIWSVPVYAVLLPI-IVFVC  85

Query:    70  KIIRRTDKTEIKEAFLAVSLALALNGVCTNTIKLIVGRPRPDFFYRCFPDGVMNSE----  125
                ++RT    ++  + L +   A+ + GV T++IK+   GRPRP+F++RCFPDG     +
Sbjct:    86  FYLKRTCVYDLHHSILGLLFAVLITGVITDSIKVATGRPRPNFYWRCFPDGKELYDALGG  145

Query:   126  MHCTGDPDLVSEGRKSFPSIHSSFAFSGLGFTTFYLAGKLHCFTESGRGKSWRLCAAILP  185
              + C G     V  EG KSFPS H+S++F+GL F +  YL+GK+  F    G       +LC    I P
Sbjct:   146  VVCHGKAAEVKEGHKSFPSGHTSWSFAGLTFLSLYLSGKIKAFNNEGHVA--KLCLVIFP  203

Query:   186  LYCAMMIALSRMCDYKHHWQDSFVGGVIGLIFAYICYRQHYP  227
              L  A ++ +SR+ DY HHWQD F G +IG + A  CYRQ YP
Sbjct:   204  LLAACLVGISRVDDYWHHWQDVFAGALIGTLVAAFCYRQFYP  245

Query : Phosphatidic acid phosphatase 29.81
Sbjct : Phosphatidic acid phosphatase
```

Fig. 1

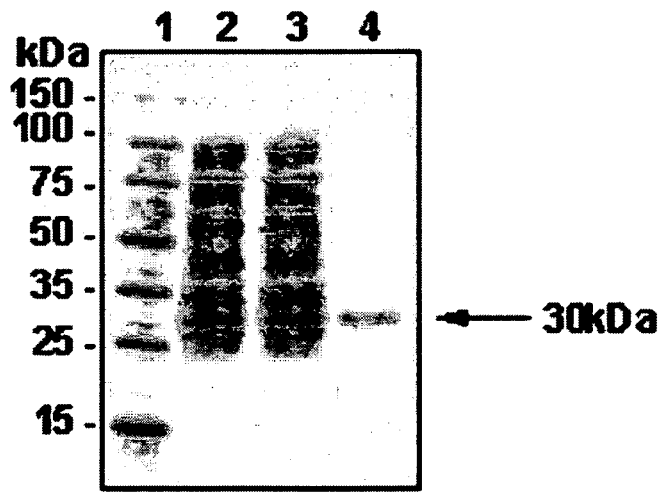

Fig. 2

POLYPEPTIDE-PHOSPHATIDIC ACID PHOSPHATASE 29.81 AND THE POLYNUCLEOTIDE ENCODING SAID POLYPEPTIDE

FIELD OF THE INVENTION

The invention relates to the field of biotechnology. In particular, the invention relates to a novel polypeptide, phosphatidic acid phosphatase 29.81, and a polynucleotide sequence encoding said polypeptide. The invention also relates to the method for the preparation and use of said polynucleotide and polypeptide.

TECHNICAL BACKGROUND phosphatidic acid (PA) and diacyl-glycerol (DG) are important molecules in the biosynthesis of membrane lipid and signal transduction. The reaction of turning phosphatidic acid into diacyl-glycerol is catalyzed by phosphatidate phosphatases (PAP), including PAP1 and PAP2. PAP1 is believed to be involved in both cytoplasm and membrane while PAP2 is strictly a membrane protein. The PAP2 gene codes for two forms of proteins, PAP2-alpha 1 and PAP2-alpha 2, by alternative splicing (DNA Cell Biol 1998; 17 (4): 377–85).

Presently, there are three isoforms of PAP2, namely PAP2a, PAP2b and PAP2c. Some research on their structure has been done, like the clarification of the site of glycosylation, the transmembrane functional domain and the catalytic site (FEBS Lett 1998 May 8; 427 (2): 188–92).

A 35 KD murine PAP2 and three human PAP2 isoforms, PAP2a, PAP2b and PAP2c, have been found. These enzymes have six transmembrane functional domains. Their catalytic sites have been preliminarily located between the second and the third outside loop. PAP2 belongs to a large group of soluble membrane binding enzymes. It has been proved that PAP2 can dephosphorize substrates such as soluble phosphatidic acid, ceramide-1-phosphate, sphingol-1-phosphate and diacyl-glycerol et al. It is thought that PAP2 has a wide substrate specificity, but this needs more experiments to support. PAP2 is shown to have the ability to regulate the metabolism of lipids derived from glyceryl and sphingolipid (Chem Phys Lipids 1999; 98 (1–2): 119–26).

The main function of phosphatidate phosphatases (PAP) is to dephosphorize phosphatidic acid to diacyl-glycerol and thus regulate the process of glyceryl lipid biosynthesis and cell signal transduction. Phosphatidate phosphatases (PAP) is an important enzyme in the metabolism process of lipids. Its substrates and products (phosphatidic acid and diacyl-glycerol) act as second messengers in signal transduction processes of living organisms. The present inventors found that cell growth, cell morphology and cytoplasm mobility during cell division are abnormal when the PAP coding gene is mutated (Biochem Biophys Res Commun. 1998; 248 (1): 87–92).

Northern result shows that the expression of PAP2 is suppressed in some tumor tissues. This phenomenon is especially striking in tumors from primary digestive tract. Thus it is deduced that PAP2 and the coding gene can be used for treatment of some tumors (DNA Cell Biol 1998; 17 (4): 377–85).

It has also been shown that PAP2 can act as a regulator of male hormone in prostatic cells. Thus PAP2 can be used for the treatment of prostate related diseases such as prostate cancer (J Biol Chem 1998; 273 (8): 4660–5); (Kai., et al. (1997) J. Biol. Chem. 272, 24572–24578).

Other research results show that PAP2 is related to the processes such as germ cell mobility, and cell division of epithelial tissue, and probably plays an important regulatory role in these processes (Biochim Biophys Acta 1997; 1348 (1–2): 56–62).

The present inventors also found that PAP is related to murine obesity. There is, however, no obvious relationship between overproduction of triglycerides and the activity of PAP based on the comparison of PAP activity in the adipose tissue of adiposis patient and normal people (Lipids 1989; 24 (12): 1048–52).

Biopsy studies showed that when compared to normal muscle tissue, the expression of PAP in nutrionally deficient muscle tissue is much lower in microsome while higher in the cytoplasm and mitochondrion (Clin Chim Acta 1985; 146 (2–3): 167–74).

The human polypeptide of the present invention shares 36% identity and 57% similarity at the amino acid sequence level with PAP. They have similar structural characteristics and belong to the same phosphatidate phosphatase protein family, and are believed to have similar biology functions. The polypeptide of the present invention is thus named phosphatidate phosphatase 29.81.

As described above, phosphatidate phosphatase 29.81 plays an essential role in the regulation of important biological functions such as cell division and embryogenesis, and it is believed that many proteins are involved in these regulations. So the determination of those related phosphatidic acid phosphatase 29.81, especially of their amino acid sequences is always desired in this field. The isolation of this novel phosphatidic acid phosphatase 29.81 forms the basis for research of the protein function under normal and clinical conditions, and this protein can be used in disease diagnosis and/or drug development.

DISCLOSURE OF THE INVENTION

One objective of the invention is to provide an isolated novel polypeptide, i.e., a phosphatidic acid phosphatase 29.81, and fragments, analogues and derivatives thereof.

Another objective of the invention is to provide a polynucleotide encoding said polypeptide.

Another objective of the invention is to provide a recombinant vector containing a polynucleotide encoding a phosphatidic acid phosphatase 29.81.

Another objective of the invention is to provide a genetically engineered host cell containing a polynucleotide encoding a phosphatidic acid phosphatase 29.81.

Another objective of the invention is to provide a method for producing a phosphatidic acid phosphatase 29.81.

Another objective of the invention is to provide an antibody against a phosphatidic acid phosphatase 29.81 of the invention.

Another objective of the invention is to provide mimetics, antagonists, agonists, and inhibitors for the polypeptide of the phosphatidic acid phosphatase 29.81.

Another objective of the invention is to provide a method for the diagnosis and treatment of diseases associated with an abnormality of phosphatidic acid phosphatase 29.81.

SUMMARY OF THE INVENTION

The present invention relates to an isolated polypeptide, which is originated from human, and comprises a polypeptide having the amino acid sequence of SEQ ID NO: 2, or its conservative mutants, or its active fragments, or its active derivatives and its analogues. Preferably, the polypeptide has preferably, the amino acid sequence of SEQ ID NO: 2.

The present invention is also related to an isolated polynucleotide, it comprises a nucleotide sequence or its variant selected from the group consisting of:

(a) the polynucleotide encoding a polypeptide comprising the amino acid sequence of SEQ ID NO.2;

(b) a polynucleotide complementary to the polynucleotide (a); and (c) a polynucleotide shares at least 70% homology to the polynucleotide (a) or (b).

More preferably, said nucleotide sequence is selected from the group consisting of (a) the sequence of position 56–871 in SEQ ID NO: 1; and (b) the sequence of position 1–1268 in SEQ ID NO: 1.

The invention also includes: a vector containing the polynucleotides of said invention, especially an expression vector; a host cell genetic engineered with the said vector, and the host cell may be obtained via transformation, transduction or transfection; a method for the production of the inventive polypeptide through the process of host cell cultivation and expression product harvest.

The invention further relates to an antibody which specifically binds to the inventive polypeptide.

The invention also includes a method for selection of compounds which simulate, activate, antagonize, or repress the activity of the phosphatidic acid phosphatase 29.81, and the compounds obtained by the method.

The invention also includes a method for in vitro assay of diseases or disease susceptibility related to the abnormal expression of phosphatidic acid phosphatase 29.81. The method involves mutation detection of the polypeptide or its polynucleotide coding sequence, or the quantitative determination or biological activity assay of the inventive polypeptide in biological samples.

The invention also includes a pharmaceutical composition which includes the inventive polypeptide, its mimetic, its agonist, its antagonist, or its repressor, and a pharmaceutically acceptable carrier.

The invention also includes application of inventive polypeptide and/or its polynucleotide for drug development to treat cancers, developmental diseases, immune diseases, or other diseases caused by abnormal expression of phosphatidic acid phosphatase 29.81.

Other aspects of the invention are apparent to the skilled in the art in view of the disclosure.

BRIEF DESCRIPTION OF THE DRAWINGS

The following drawings are provided to illustrate the embodiment of the invention, not to limit the scope of invention defined by the claims.

FIG. 1 shows an alignment comparison of amino acid sequences of phosphatidic acid phosphatase 29.81 of the invention and phosphatidic acid phosphatase. The upper sequence is phosphatidic acid phosphatase 29.81, and the lower sequence is phosphatidic acid phosphatase. The identical and similar amino acids are indicated by a one-letter code of amino acid and "+" respectively.

FIG. 2 shows the SDS-PAGE of the isolated phosphatidic acid phosphatase 29.81 which has a molecular weight of 29.81 kDa. The isolated protein band is marked with an arrow.

DESCRIPTION OF THE INVENTION

The terms used in this specification and claims have the following meanings, unless specifically noted otherwise.

"Nucleotide sequence" refers to oligonucleotide, nucleotide, or polynucleotide and parts of a polynucleotide. It also refers to genomic or synthetic DNA or RNA, which could be single stranded or double stranded, and could represent the sense strand or the antisense strand. Similarly, the term "amino acid sequence" refers to oligopeptide, peptide, polypeptide, or protein sequence and parts of proteins. When the "amino acid sequence" in said invention is related to the sequence of a natural protein, the amino acid sequence of said "peptide" or "protein" will not be limited to be identical to the sequence of that natural protein.

"Variety" or "variant" of a protein or polynucleotide refers to the amino acid sequence with one or several amino acid changed, or its encoding polynucleotide sequence with one or several nucleotides changed. Such changes include deletion, insertion, or substitution of one or more amino acids in the animo acid sequence, or of nucleotides in the polynucleotide sequence. These changes could be conservative and the substituted amino acid has similar structure or chemical characteristics as the original one, just as the substitution of Ile with Leu. Changes also could be not conservative, just as the substitution of Ala with Trp.

"Deletion" refers to the deletion of one or more amino acids in the amino acid sequence, or of one or more nucleotides in the nucleotide sequence.

"Insertion" or "addition" refers to the addition of one or several amino acids in the amino acid sequence, or of one or several nucleotides in the nucleotide sequence, comparing to the natural molecule. "Substitution" refers to the change of one or several amino acids, or of one or several nucleotides, into different ones without changing their number.

"Biological activity" refers to a protein with a natural structural, regulatory or biochemical functions. Similarly, the term "immunologic competence" refers to the ability of natural, recombinant, or synthetic proteins to induce a specific immune reaction, or to bind specific antibodies in an appropriate animal or cell.

"Agonist" refers to the molecule which could regulate the activity of phosphatidic acid phosphatase 29.81 by binding to or otherwise changing it. Agonists include proteins, nucleotides, carbohydrates or any other molecules which could bind to the phosphatidic acid phosphatase 29.81.

"Antagonist" or "repressor" refers to the molecules which could repress or downregulate the biological activity or immune activity of phosphatidic acid phosphatase 29.81 when bound to it. Antagonists or repressors include proteins, nucleotides, carbohydrates or any other molecules which could bind the phosphatidic acid phosphatase 29.81.

"Regulation" refers to a functional change of phosphatidic acid phosphatase 29.81, including increase or decrease of the protein activity, changes in binding specifity, changes of any other biological, functional or immune characteristics of phosphatidic acid phosphatase 29.81.

"Substantially pure" refers to the condition of purity without any other natural related proteins, lipids, saccharides, or other substances. Ordinarily skilled artisans in this field can purify phosphatidic acid phosphatase 29.81 by standard protein purification techniques. Substantially pure phosphatidic acid phosphatase 29.81 produces a single main band in denaturing polyacrylamide gel. The purity of phosphatidic acid phosphatase 29.81 can also be analyzed by amino acid sequence analysis.

"Complementary" or "complementation" refers to the natural conjugation of polynucleotides by base pairing under the condition of suitable ion concentration and temperature. For instance, the sequence "C-T-G-A" could bind to its complementary sequence "G-A-C-T." The complementation between two single strand molecules could be partial or complete. Complementary degree between two single strands has obvious influence on hybrid efficiency and intensity of the nucleotides.

"Homology" refers to the complementary degree, which may be partially or completely homologous. "Partial homology" refers to a partially complementary sequence when compared to a target nucleotide, and the sequence could at least partially repress the hybridization between a completely complementary sequence and the target nucleotide. Repression of the hybridization could be assayed by hybridization (Southern blot or Northern blot) under a lower stringency condition. Substantially complementary sequence or hybrid probe could compete with the completely complementary sequence and repress its hybridization with the target sequence under a lower stringency condition. This effect does not mean that nonspecific binding is allowed under a lower stringency condition, because specific or selective reaction is still required for hybridization under a lower stringency condition.

"Identity percentage" or "percent identity" refers to the percentage of sequence identity or similarity when two or several kinds of amino acid or nucleotide sequences are compared. Identity percentage could be determined by computational methods such as the MEGALIGN program (Lasergene software package, DNASTAR, Inc., Madison Wis.). MEGALIGN program can compare two or several sequences with different kinds of methods such as Cluster method (Higgins, D. G. And P. M. Sharp (1988) Gene 73: 237–244). Cluster method examines the distance between all pairs and arranges the sequences into clusters. Then the clusters are partitioned by pair or group. The identity percentage between two amino acid sequences, A and B, can be calculated by the following equation:

$$\frac{\text{Number of paired residues between sequence } A \text{ and } B}{\text{Residue number of sequence } A - \text{number of spacing residues in sequence } A - \text{number of spacing residue in sequence } B} \times 100$$

Identity percentage between nucleotide sequences can also be determined by the Cluster method or other well-known methods in this field such as the Jotun Hein method (Hein J., (1990) Methods in Emzymology 183: 625–645)

"Similarity" refers to the identical degree or conservative substitution degree of amino acid residues in corresponding sites of the amino acid sequences when compared to each other. Amino acids for conservative substitution are: e.g. among negative charged amino acids (e.g. Asp and Glu); among positive charged amino acids (including Leu, Ile and Val); between Gly and Ala; between Asn and Gin; between Ser and Thr; and between Phe and Tyr.

"Antisense" refers to the nucleotide sequences complementary to a specific DNA or RNA sequence. "antisense strand" refers to the nucleotide strand complementary to the "sense strand."

"Derivative" refers to HFP or the chemically modified nucleotide encoding it. This kind of modified chemical can be derived from replacement of the hydrogen atom with an alkyl, acyl, or amino group. The nucleotide derivative can encode peptide remaining the major biological characteristics of the natural molecule.

"Antibody" refers to an intact antibody or its fragments such as Fa, F (ab')$_2$ and Fv, and it can specifically bind antigenic determinants of phosphatidic acid phosphatase 29.81.

"Humanized antibody" refers to an antibody which has its amino acid sequence in non-antigen binding region replaced to mimic human antibody and still retain the original binding activity.

The term "isolated" refers to the removal of a material out of its original environment (for instance, if it is naturally produced, original environment refers to its natural environment). For example, a naturally produced polynucleotide or a peptide in a living organism means it has not been "isolated." While the separation of the polynucleotide or a peptide from its coexisting materials in natural system means it is "isolated." This polynucleotide may be a part of a vector. This polynucleotide or peptide may also be part of a compound. Since the vector or compound is not part of its natural environment, the polynucleotide or peptide is still "isolated".

As used herein, the term "isolated" refers to a substance which has been isolated from the original environment. For naturally occurring substance, the original environment is the natural environment. For example, the polynucleotide and polypeptide in a naturally occurring state in the viable cells are not isolated or purified. However, if the same polynucleotide and polypeptide have been isolated from other components naturally accompanying them, they are isolated or purified.

As used herein, "isolated phosphatidic acid phosphatase 29.81," means that phosphatidic acid phosphatase 29.81, does not essentially contain other proteins, lipids, carbohydrates or any other substances associated therewith in nature. Those skilled in the art can purify phosphatidic acid phosphatase 29.81, by standard protein purification techniques. The purified polypeptide forms a single main band on a non-reductive PAGE gel. The purity of phosphatidic acid phosphatase 29.81 can be analyzed by amino acid sequence analysis.

The invention provides a novel polypeptide-phosphatidic acid phosphatase 29.81, which comprises the amino acid sequence shown in SEQ ID NO: 2. The polypeptide of the invention may be a recombinant polypeptide, natural polypeptide, or synthetic polypeptide, preferably a recombinant polypeptide. The polypeptide of the invention may be a purified natural product or a chemically synthetic product. Alternatively, it may be produced from prokaryotic or eukaryotic hosts, such as bacterial, yeast, higher plant, insect, and mammalian cells, using recombinant techniques. Depending on the host used in the protocol of recombinant production, the polypeptide of the invention may be glycosylated or non-glycosylated. The polypeptide of the invention may or may not comprise the starting Met residue.

The invention further comprises fragments, derivatives and analogues of phosphatidic acid phosphatase 29.81. As used in the invention, the terms "fragment", "derivative" and "analogue" mean the polypeptide that essentially retains the same biological functions or activity of phosphatidic acid phosphatase 29.81 of the invention. The fragment, derivative or analogue of the polypeptide of the invention may be (i) one in which one or more of the amino acid residues are substituted with a conserved or non-conserved amino acid residue (preferably a conserved amino acid residue) and such substituted amino acid residue may or may not be one encoded by the genetic code; or (ii) one in which one or more of the amino acid residues are substituted with other residues, including a substituent group; or (iii) one in which the mature polypeptide is fused with another compound, such as a compound to increase the half-life of the polypeptide (for example, polyethylene glycol); or (iv) one in which additional amino acids are fused to the mature polypeptide, such as a leader or secretory sequence or a sequence which is employed for purification of the mature polypeptide or a proprotein sequence. Such fragments, derivatives and analogs are deemed to be within the scope of the skilled in the art from the teachings herein.

The invention provides an isolated nucleic acid or polynucleotide which comprises the polynucleotide encoding an amino acid sequence of SEQ ID NO: 2. The polynucleotide sequence of the invention includes the nucleotide sequence of SEQ ID NO: 1. The polynucleotide of the invention was identified in a human embryonic brain cDNA library. Preferably, it comprises a full-length polynucleotide sequence of 1268 bp, whose ORF (56–871) encodes 271 amino acids. Based on amino acid homology comparison, it is found that the encoded polypeptide is 36% homologous to phosphatidic acid phosphatase. This novel phosphatidic acid phosphatase 29.81 has similar structures and biological functions to those of the phosphatidic acid phosphatase.

The polynucleotide according to the invention may be in the forms of DNA or RNA. The forms of DNA include cDNA, genomic DNA, and synthetic DNA, etc., in single stranded or double stranded form. DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein or peptide comprising a sequence of SEQ ID NO: 2 and which has a nucleotide sequence different from the sequence of coding region in SEQ ID NO: 1.

The polynucleotide encoding the mature polypeptide of SEQ ID NO: 2 includes those encoding only the mature polypeptide, those encoding mature polypeptide plus various additional coding sequence, the coding sequence for mature polypeptide (and optional additional encoding sequence) plus the non-coding sequence.

The term "polynucleotide encoding the polypeptide" includes polynucleotides encoding said polypeptide and polynucleotides comprising additional coding and/or non-coding sequences.

The invention further relates to variants of the above polynucleotides which encode a polypeptide having the same amino acid sequence of invention, or a fragment, analogue and derivative of said polypeptide. The variant of the polynucleotide may be a naturally occurring allelic variant or a non-naturally occurring variant. Such nucleotide variants include substitution, deletion, and insertion variants. As known in the art, an allelic variant may have a substitution, deletion, and insertion of one or more nucleotides without substantially changing the functions of the encoded polypeptide.

The present invention further relates to polynucleotides, which hybridize to the above-described sequences, that is, there is at least 50% and preferably at least 70% identity between the sequences. The present invention particularly relates to polynucleotides, which hybridize to the polynucleotides of the invention under stringent conditions. As herein used, the term "stringent conditions" means the following conditions: (1) hybridization and washing under low ionic strength and high temperature, such as 0.2×SSC, 0.1% SDS, 60° C.; or (2) hybridization after adding denaturants, such as 50% (v/v) formamide, 0.1% bovine serum/0.1% Ficoll, 42° C.; or (3) hybridization only when the homology of two sequences at least 95%, preferably 97%. Further, the polynucleotides which hybridize to the hereinabove described polynucleotides encode a polypeptide which retains the same biological function and activity as the mature polypeptide of SEQ ID NO: 2

The invention also relates to nucleic acid fragments hybridized with the herein above sequence. As used in the present invention, the length of the "nucleic acid fragment" is at least more than 10 bp, preferably at least 20–30 bp, more preferably at least 50–60 bp, and most preferably at least 100 bp. The nucleic acid fragment can be used in amplification techniques of nucleic acid, such as PCR, so as to determine and/or isolate the polynucleotide encoding phosphatidic acid phosphatase 29.81.

The polypeptide and polynucleotide of the invention are preferably in the isolated form, preferably purified to be homogenous.

According to the invention, the specific nucleic acid sequence encoding phosphatidic acid phosphatase 29.81 can be obtained in various ways. For example, the polynucleotide is isolated by hybridization techniques well-known in the art, which include, but are not limited to 1) the hybridization between a probe and genomic or cDNA library so as to select a homologous polynucleotide sequence, and 2) antibody screening of expression library so as to obtain polynucleotide fragments encoding polypeptides having common structural features.

According to the invention, DNA fragment sequences may further be obtained by the following methods: 1) isolating double-stranded DNA sequence from genomic DNA; and 2) chemical synthesis of DNA sequence so as to obtain the double-stranded DNA.

Among the above methods, the isolation of genomic DNA is least frequently used. A commonly used method is the direct chemical synthesis of DNA sequence. A more frequently used method is the isolation of cDNA sequence. Standard methods for isolating the cDNA of interest is to isolate mRNA from donor cells that highly express said gene followed by reverse transcription of mRNA to form plasmid or phage cDNA library. There are many established techniques for extracting mRNA and the kits are commercially available (e.g. Qiagene). Conventional method can be used to construct cDNA library (Sambrook, et al., *Molecular Cloning*, A Laboratory Manual, Cold Spring Harbor Laboratory. New York, 1989). The cDNA libraries are also commercially available. For example, Clontech Ltd. has various cDNA libraries. When PCR is further used, even an extremely small amount of expression products can be cloned.

Numerous well-known methods can be used for screening for the polynucleotide of the invention from cDNA library. These methods include, but are not limited to, (1) DNA-DNA or DNA-RNA hybridization; (2) the appearance or loss of the function of the marker-gene; (3) the determination of the level of phosphatidic acid phosphatase 29.81 transcripts; (4) the determination of protein product of gene expression by immunology methods or the biological activity assays. The above methods can be used alone or in combination.

In method (1), the probe used in the hybridization could be homologous to any portion of polynucleotide of invention. The length of probe is typically at least 10 nucleotides, preferably at least 30 nucleotides, more preferably at least 50 nucleotides, and most preferably at least 100 nucleotides. Furthermore, the length of the probe is usually less than 2000 nucleotides, preferably less than 1000 nucleotides. The probe usually is the DNA sequence chemically synthesized on the basis of the sequence information. Of course, the gene of the invention itself or its fragment can be used as a probe. The labels for DNA probe include, e.g., radioactive isotopes, fluoresceins or enzymes such as alkaline phosphatase.

In method (4), the detection of the protein products expressed by phosphatidic acid phosphatase 29.81 gene can be carried out by immunological methods, such as Western blotting, radioimmunoassay, and ELISA.

The method of amplification of DNA/RNA by PCR (Saiki, et al. Science 1985; 230: 1350–1354) is preferably used to obtain the polynucleotide of the invention. When it is difficult to obtain the full-length cDNA, the method of RACE (RACE—cDNA terminate rapid amplification) is preferably used. The primers used in PCR can be selected according to the polynucleotide sequence information of the invention disclosed herein, and can be synthesized by conventional methods. The amplified DNA/RNA fragments can be isolated and purified by conventional methods such as gel electrophoresis.

Sequencing of polynucleotide sequence of the gene of the invention or its various DNA fragments can be carried out by the conventional dideoxy sequencing method (Sanger et al. PNAS, 1977, 74: 5463–5467). Sequencing of polynucleotide sequence can also be carried out using the commercially available sequencing kits. In order to obtain the full-length cDNA sequence, it is necessary to repeat the sequencing process. Sometimes, it is needed to sequence the cDNA of several clones to obtain the full-length cDNA sequence.

The invention further relates to a vector comprising the polynucleotide of the invention, a genetically engineered host cell transformed with the vector of the invention or directly with the sequence encoding phosphatidic acid phosphatase 29.81, and a method for producing the polypeptide of the invention by recombinant techniques.

In the present invention, the polynucleotide sequences encoding phosphatidic acid phosphatase 29.81 may be inserted into a vector to form a recombinant vector containing the polynucleotide of the invention. The term "vector" refers to a bacterial plasmid, bacteriophage, yeast plasmid, plant virus or mammalian virus such as adenovirus, retrovirus or any other vehicle known in the art. Vectors suitable for use in the present invention include, but are not limited to the T7-based expression vector for expression in bacteria (Rosenberg, et al., Gene, 56: 125, 1987), The pMSXND expression vector for expression in mammalian cells (Lee and Nathans, J. Biol. Chem., 263: 3521, 1988) and baculovirus-derived vectors for expression in insect cells. Any plasmid or vector can be used to construct the recombinant expression vector as long as it can replicate and is stable in the host. One important feature of an expression vector is that the expression vector typically contains an origin of replication, a promoter, a marker gene as well as translation regulatory components.

Methods known in the art can be used to construct an expression vector containing the DNA sequence of phosphatidic acid phosphatase 29.81 and appropriate transcription/translation regulatory components. These methods include in vitro recombinant DNA technique, DNA synthesis technique, in vivo recombinant technique and so on (Sambroook, et al. *Molecular Cloning*, a Laboratory Manual, cold Spring Harbor Laboratory. New York, 1989). The DNA sequence is operatively linked to a proper promoter in an expression vector to direct the synthesis of mRNA. Exemplary promoters are lac or trp promoter of *E. coli*; PL promoter of λ phage; eukaryotic promoters including CMV immediate early promoter, HSV thymidine kinase promoter, early and late SV40 promoter, LTRs of retrovirus, and other known promoters which control gene expression in the prokaryotic cells, eukaryotic cells or viruses. The expression vector may further comprise a ribosome binding site for initiating translation, transcription terminator and the like. Transcription in higher eukaryotes is increased by inserting an enhancer sequence into the vector. Enhancers are cis-acting elements of DNA, usually about from 10 to 300 bp in length that act on a promoter to increase gene transcription level. Examples include the SV40 enhancer on the late side of the replication origin 100 to 270 bp, the polyoma enhancer on the late side of the replication origin, and adenovirus enhancers.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for *E. coli*.

The skilled in the art know clearly how to select appropriate vectors, transcriptional regulatory elements, e.g., promoters, enhancers, and selective marker genes.

According to the invention, polynucleotide encoding phosphatidic acid phosphatase 29.81 or recombinant vector containing said polynucleotide can be transformed or transfected into host cells to construct genetically engineered host cells containing said polynucleotide or said recombinant vector. The term "host cell" means prokaryote, such as bacteria; or primary eukaryote, such as yeast; or higher eukaryotic, such as mammalian cells. Representative examples are bacterial cells, such as *E. coli*, Streptomyces, *Salmonella typhimurium*; fungal cells, such as yeast; plant cells; insect cells such as Drosophila S2 or Sf9; animal cells such as CHO, COS or Bowes melanoma.

Transformation of a host cell with the DNA sequence of invention or a recombinant vector containing said DNA sequence may be carried out by conventional techniques as are well known to those skilled in the art. When the host is prokaryotic, such as *E. coli*, competent cells, which are capable of DNA uptake, can be prepared from cells harvested after exponential growth phase and subsequently treated by the CaCl$_2$ method using procedures well known in the art. Alternatively, MgCl$_2$ can be used. Transformation can also be carried out by electroporation, if desired. When the host is a eukaryote, transfection methods as well as calcium phosphate precipitation may be used. Conventional mechanical procedures such as micro-injection, electroporation, or liposome-mediated transfection may also be used.

The recombinant phosphatidic acid phosphatase 29.81 can be expressed or produced by the conventional recombinant DNA technology (Science, 1984; 224: 1431), using the polynucleotide sequence of the invention. The steps generally include:

(1) transfecting or transforming the appropriate host cells with the polynucleotide (or variant) encoding human phosphatidic acid phosphatase 29.81 of the invention or the recombinant expression vector containing said polynucleotide;

(2) culturing the host cells in an appropriate medium; and (3) isolating or purifying the protein from the medium or cells.

In Step (2) above, depending on the host cells used, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In Step (3), the recombinant polypeptide may be included in the cells, or expressed on the cell membrane, or secreted out of the cell. If desired, physical, chemical and other properties can be utilized in various isolation methods to isolate and purify the recombinant protein. These methods are well-known to those skilled in the art and include, but are not limited to conventional renaturation treatment, treatment by a protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatagraphy, and a combination thereof.

The polypeptide of the invention and antagonists, agonists and inhibitors thereof can be directly used for the treatment of diseases, e.g., various malignant tumors or cancers, dermatitis, inflammation, adrenoprival disease and HIV infection and immune system diseases.

Human phosphatidate phosphatase plays an important role in signal transduction in vivo and cell membrane lipid biosynthesis. Phosphatidate phosphatase (PAP) turns phosphatidic acid (PA) into diacyl-glycerol (DG) and regulates the biosynthesis of glyceryl lipids. PAP2 is related to tumor genesis and male hormone regulation. The abnormal expression of human phosphatidate phosphatase will cause corresponding abnormal metabolism of phospholipid and triglyceride and then lead to related diseases.

The human polypeptide in this invention and human phosphatidate phosphatase protein have similar biologic function and have characteristic sequence of phosphatidate phosphatase family, which they belong to. The abnormal expression of this polypeptide will cause abnormal metabolism of phospholipid and triglyceride and then lead to related diseases.

A. Phospholipid is an important component of cell membrane, nuclear membrane and nerve myelin sheath membrane. Related diseases include:
  a. Demyelinating peripheral neuropathy: Limb paralysis, limb sensory disturbance, respiratory paralysis (intercostal muscle, diaphragm myoparalysis), facial paralysis, medulla oblongata paralysis (hoarseness, cough), vegetative nerve symptom (increased sweating, skin flush, tachycardia, orthostatic hypotension, urine staying), incoordination, mental disorder, etc.
  b. Leukodystrophy (demyelination) diseases: metachromatic leukodystrophy, Pelizaeus-Merzbach disease, Alexander disease, Cockaynes syndrome, etc.

B. Because phospholipid contains both hydrophilic groups and hydrophobic groups, it can emulsify triglyceride and fat-soluble vitamins and promote their absorption and transportation. Related diseases include:
  a. Fat-soluble vitamin deficiency: $V_A$ (nyctalopia, xerophthalmia, bones growth retardation), $V_E$ (infertility, abortion, anemia, amyotrophy, nerve degeneration), $V_K$ (deficiency of blood clotting factor II, VII, IX, X), $V_{D3}$ (child rickets, adult osteomalacia, kidney stones) et al.
  b. Hypertriglyceridemia: liparitosis (fatty liver, fat deposition cardiomyopathy, fat deposition nephrotic syndrome) and related tumors (lipoma, lipoblastoma, liposarcoma) et al.

C. There are many unsaturated fatty acids in phospholipid, including essential fatty acids linoleic acids, linolenic acids, and arachidonic acid. Arachidonic acid is the material for synthesis of prostaglandin. Related diseases include:
Prostaglandin and related functional disorders: Hemorrhagic diseases and coagulopathy (thromboxane $A_2$), bronchial asthma ($PGE_2/PGF_2$), peptic ulcer ($PGE_2$), Uterine dyscontraction-abortion et al.

In addition, dysfunction of human phosphatidate phosphatase can also lead to tumor genesis.

As mentioned above, the polypeptide of the present invention and its antagonists, agonists and inhibitors can be directly applied in the treatment of various diseases such as demyelinated peripheral neuropathy, nyctalopia, rickets, fatty liver, bronchial asthma, and peptic ulcer.

The invention also provides methods for screening compounds so as to identify an agent which enhances phosphatidic acid phosphatase 29.81 activity (agonists) or decrease phosphatidic acid phosphatase 29.81 activity (antagonists). The agonists enhance the biological functions of phosphatidic acid phosphatase 29.81 such as inactivation of cell proliferation, while the antagonists prevent and cure the disorders associated with the excess cell proliferation, such as various cancers. For example, in the presence of an agent, the mammal cells or the membrane preparation expressing phosphatidic acid phosphatase 29.81 can be incubated with the labeled phosphatidic acid phosphatase 29.81 to determine the ability of the agent to enhance or repress the interaction.

Antagonists of phosphatidic acid phosphatase 29.81 include antibodies, compounds, receptor deletants and analogues. The antagonists of phosphatidic acid phosphatase 29.81 can bind to phosphatidic acid phosphatase 29.81 and eliminate or reduce its function, or inhibit the production of phosphatidic acid phosphatase 29.81, or bind to the active site of said polypeptide so that the polypeptide can not function biologically.

When screening for compounds as an antagonist, phosphatidic acid phosphatase 29.81 may be added into a biological assay. It can be determined whether the compound is an antagonist or not by determining its effect on the interaction between phosphatidic acid phosphatase 29.81 and its receptor. Using the same method as that for screening compounds, receptor deletants and analogues acting as antagonists can be selected. Polypeptide molecules capable of binding to phosphatidic acid phosphatase 29.81 can be obtained by screening a polypeptide library comprising various combinations of amino acids bound onto a solid matrix. Usually, phosphatidic acid phosphatase 29.81 is labeled in the screening.

The invention further provides a method for producing antibodies using the polypeptide, and its fragment, derivative, analogue or cells as an antigen. These antibodies may be polyclonal or monoclonal antibodies. The invention also provides antibodies against epitopes of phosphatidic acid phosphatase 29.81. These antibodies include, but are not limited to, polyclonal antibody, monoclonal antibody, chimeric antibody, single-chain antibody, Fab fragment and the fragments produced by a Fab expression library.

Polyclonal antibodies can be prepared by immunizing animals, such as rabbit, mouse, and rat, with phosphatidic acid phosphatase 29.81. Various adjuvants, including but are not limited to Freund's adjuvant, can be used to enhance the immunization. The techniques for producing phosphatidic acid phosphatase 29.81 monoclonal antibodies include, but are not limited to, the hybridoma technique (Kohler and Milstein. Nature, 1975, 256: 495–497), the trioma technique, the human B-cell hybridoma technique, the EBV-hybridoma technique and so on. A chimeric antibody comprising a constant region of human origin and a variable region of non-human origin can be produced using methods well-known in the art (Morrison et al, PNAS, 1985, 81: 6851). Furthermore, techniques for producing a single-chain antibody (U.S. Pat. No. 4,946,778) are also useful for preparing single-chain antibodies against phosphatidic acid phosphatase 29.81.

The antibody against phosphatidic acid phosphatase 29.81 can be used in immunohistochemical method to detect the presence of phosphatidic acid phosphatase 29.81 in a biopsy specimen.

Monoclonal antibodies specific to phosphatidic acid phosphatase 29.81 can be labeled by radioactive isotopes, and injected into human body to trace the location and distribution of phosphatidic acid phosphatase 29.81. This radioactively labeled antibody can be used in the non-wounding diagnostic method for the determination of tumor location and metastasis.

Antibodies can also be designed as an immunotoxin targeting a particular site in the body. For example, a monoclonal antibody having high affinity to phosphatidic acid phosphatase 29.81 can be covalently bound to bacterial or plant toxins, such as diphtheria toxin, ricin, ormosine. One common method is to challenge the amino group on the antibody with sulfydryl cross-linking agents, such as SPDP, and bind the toxin onto the antibody by interchanging the disulfide bonds. This hybrid antibody can be used to kill phosphatidic acid phosphatase 29.81-positive cells.

The antibody of the invention is useful for the therapy or the prophylaxis of disorders related to the phosphatidic acid phosphatase 29.81. The appropriate amount of antibody can be administrated to stimulate or block the production or activity of phosphatidic acid phosphatase 29.81.

The invention further provides diagnostic assays for quantitative and in situ measurement of phosphatidic acid phosphatase 29.81 level. These assays are well known in the art and include FISH assay and radioimmunoassay. The level of phosphatidic acid phosphatase 29.81 detected in the assay can be used to illustrate the importance of phosphatidic acid phosphatase 29.81 in diseases and to determine the diseases associated with phosphatidic acid phosphatase 29.81.

The polypeptide of the invention is useful in the analysis of polypeptide profile. For example, the polypeptide can be specifically digested by physical, chemical, or enzymatic means, and then analyzed by one, two or three dimensional gel electrophoresis, preferably by spectrometry.

New phosphatidic acid phosphatase 29.81 polynucleotides also have many therapeutic applications. Gene therapy technology can be used in the therapy of abnormal cell proliferation, development or metabolism, which are caused by the loss of phosphatidic acid phosphatase 29.81 expression or the abnormal or non-active expression of phosphatidic acid phosphatase 29.81. Recombinant gene therapy vectors, such as virus vectors, can be designed to express mutated phosphatidic acid phosphatase 29.81 so as to inhibit the activity of endogenous phosphatidic acid phosphatase 29.81. For example, one form of mutated phosphatidic acid phosphatase 29.81 is a truncated phosphatidic acid phosphatase 29.81 whose signal transduction domain is deleted. Therefore, this mutated phosphatidic acid phosphatase 29.81 can bind the downstream substrate without the activity of signal transduction. Thus, the recombinant gene therapy vectors can be used to cure diseases caused by abnormal expression or activity of phosphatidic acid phosphatase 29.81. The expression vectors derived from a virus, such as retrovirus, adenovirus, adenoassociated virus, herpes simplex virus, parvovirus, and so on, can be used to introduce the phosphatidic acid phosphatase 29.81 gene into the cells. The methods for constructing a recombinant virus vector harboring phosphatidic acid phosphatase 29.81 gene are described in the literature (Sambrook, et al. supra). In addition, the recombinant phosphatidic acid phosphatase 29.81 gene can be packed into liposome and then transferred into the cells.

The methods for introducing the polynucleotides into tissues or cells include directly injecting the polynucleotides into tissue in the body; or introducing the polynucleotides into cells in vitro with vectors, such as virus, phage, or plasmid, etc, and then transplanting the cells into the body.

Also included in the invention are ribozymes and the oligonucleotides, including antisense RNA and DNA, which inhibit the translation of the phosphatidic acid phosphatase 29.81 mRNA. Ribozyme is an enzyme-like RNA molecule capable of specifically cutting certain RNA. The mechanism is nucleic acid endo-cleavage following specific hybridization of ribozyme molecule and the complementary target RNA. Antisense RNA and DNA as well as ribozyme can be prepared by using any conventional techniques for RNA and DNA synthesis, e.g., the widely used solid phase phosphite chemical method for oligonucleotide synthesis. Antisense RNA molecule can be obtained by the in vivo or in vitro transcription of the DNA sequence encoding said RNA, wherein said DNA sequence is integrated into the vector and downstream of the RNA polymerase promoter. In order to increase its stability, a nucleic acid molecule can be modified in many manners, e.g., increasing the length of two the flanking sequences, replacing the phosphodiester bond with the phosphothioester bond in the oligonucleotide.

The polynucleotide encoding phosphatidic acid phosphatase 29.81 can be used in the diagnosis of phosphatidic acid phosphatase 29.81 related diseases. The polynucleotide encoding phosphatidic acid phosphatase 29.81 can be used to detect whether phosphatidic acid phosphatase 29.81 is expressed or not, and whether the expression of phosphatidic acid phosphatase 29.81 is normal or abnormal in the case of diseases. For example, phosphatidic acid phosphatase 29.81 DNA sequences can be used in the hybridization with biopsy samples to determine the expression of phosphatidic acid phosphatase 29.81. The hybridization methods include Southern blotting, Northern blotting and in situ blotting, etc., which are well-known and established techniques. The corresponding kits are commercially available. A part of or all of the polynucleotides of the invention can be used as probe and fixed on a microarray or DNA chip for analysis of differential expression of genes in tissues and for the diagnosis of genes. The phosphatidic acid phosphatase 29.81 specific primers can be used in RNA-polymerase chain reaction and in vitro amplification to detect transcripts of phosphatidic acid phosphatase 29.81.

Further, detection of mutations in phosphatidic acid phosphatase 29.81 gene is useful for the diagnosis of phosphatidic acid phosphatase 29.81-related diseases. Mutations of phosphatidic acid phosphatase 29.81 include site mutation, translocation, deletion, rearrangement and any other mutations compared with the wild-type phosphatidic acid phosphatase 29.81 DNA sequence. The conventional methods, such as Southern blotting, DNA sequencing, PCR and in situ blotting, can be used to detect a mutation. Moreover, mutations sometimes affects the expression of protein. Therefore, Northern blotting and Western blotting can be used to indirectly determine whether the gene is mutated or not.

Sequences of the present invention are also valuable for chromosome identification. The sequence is specifically targeted to and can hybridize with a particular location on an individual human chromosome. There is a current need for identifying particular sites of gene on the chromosome. Few chromosome marking reagents based on actual sequence data (repeat polymorphism) are presently available for marking chromosomal location. The mapping of DNA to chromosomes according to the present invention is an important first step in correlating those sequences with genes associated with disease.

Briefly, sequences can be mapped to chromosomes by preparing PCR primers (preferably 15–35 bp) from the cDNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the oligonucleotide primers of the invention, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clones to a metaphase chromosomal spread can be used to provide a precise chromosomal location in one step. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis.

Next, it is necessary to determine the differences in the cDNA or genomic sequence between affected and unaffected individuals. If a mutation is observed in some or all of the affected individuals but not in any normal individuals, then the mutation is likely to be the cause of the disease. Comparison of affected and unaffected individuals generally involves first looking for structural alterations in the chromosomes, such as deletions or translocations, that are visible from chromosome level, or detectable using PCR based on that DNA sequence. With current resolution of physical mapping and genetic mapping techniques, a cDNA precisely localized to a chromosomal region associated with the disease could be one of 50 to 500 potential causative genes. (This assumes 1 megabase mapping resolution and one gene per 20 kb).

According to the invention, the polypeptides, polynucleotides and its mimetics, agonists, antagonists and inhibitors may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient with no influence on the effect of the drug. These compositions can be used as drugs in disease treatment.

The invention also provides a pharmaceutical pack or kit comprising one or more containers filled with one or more of the ingredients of the pharmaceutical compositions of the invention. With such container(s) there may be a notice from a government agency, that regulates the manufacture, use or sale of pharmaceuticals or biological products, the notice reflects government's approval for the manufacture, use or sale for human administration. In addition, the polypeptides of the invention may be employed in conjunction with other therapeutic compounds.

The pharmaceutical compositions may be administered in a convenient manner, such as through topical, intravenous, intraperitoneal, intramuscular, subcutaneous, intranasal or intradermal routes, phosphatidic acid phosphatase 29.81 is administered in an amount, which is effective for treating and/or prophylaxis of the specific indication. The amount of phosphatidic acid phosphatase 29.81 administrated on patient will depend upon various factors, such as delivery methods, the subject health, the judgment of the skilled clinician.

BEST MODE FOR CARRYING OUT THE INVENTION

The invention is further illustrated by the following examples. It is appreciated that these examples are only intended to illustrate the invention, not to limit the scope of the invention. For the experimental methods in the following examples, they are performed under routine conditions, e.g., those described by Sambrook. et al., in *Molecule Clone*: A Laboratory Manual, New York: Cold Spring Harbor Laboratory Press, 1989, or as instructed by the manufacturers, unless otherwise specified.

EXAMPLE 1

Cloning of Phosphatidic Acid Phosphatase 29.81 Gene

Total RNA from a human embryonic brain was extracted by the one-step method with guanidinium isocyanate/phenol/chloroform. The poly (A) mRNA was isolated from the total RNA with Quik mRNA Isolation Kit (Qiegene). cDNA was prepared by reverse transcription with 2 μg poly (A) mRNA. The cDNA fragments were inserted into the polyclonal site of pBSK (+) vector (Clontech) using Smart cDNA cloning kit (Clontech) and then transformed into DH5α to form the cDNA library. The 5'- and 3'-ends of all clones were sequenced with Dye terminate cycle reaction sequencing kit (Perkin-Elmer) and ABI 377 Automatic Sequencer (Perkin-Elmer). The sequenced cDNA were compared with the public database of DNA sequences (Genebank) and the DNA sequence of one clone 2933e11 was found to be a novel DNA sequence. The inserted cDNA sequence of clone 2933e11 was dual-directionally sequenced with a serial of synthesized primers. It was indicated that the full length cDNA contained in clone 2933e11 was 1268 bp (SEQ ID NO: 1) with a 816 bp ORF located in positions 56–871 bp which encoded a novel protein (SEQ ID NO: 2). This clone was named pBS-2933e11 and the encoded protein was named phosphatidic acid phosphatase 29.81.

EXAMPLE 2

Homology Search of cDNA Clone

The homology research of the DNA sequence and its protein sequence of phosphatidic acid phosphatase 29.81 of the invention were performed by Blast (Basic local Alignment search tool) (Altschul, S F et al. J. Mol. Biol., 1990; 215: 403–10) in databases such as Genbank, Swissport, etc. The most homologous gene to phosphatidic acid phosphatase 29.81 of the invention is known phosphatidic acid phosphatase. The Genbank accession number of its encoded protein is AC006200. The alignment result of the protein was shown in FIG. 1. Two proteins are highly homologous with an identity of 36% and a similarity of 57%.

EXAMPLE 3

Cloning Phosphatidic Acid Phosphatase 29.81 Gene by RT-PCR

The template was total RNA extracted from a human embryonic brain. The reverse transcription was carried out with oligo-dT primer to produce cDNAs. After cDNA purified with Qiagen Kit, PCR was carried out with the following primers:

```
Primer 1:
5'-GGCGGGAGCCGCGGAGAGCACCAG-3'     (SEQ ID NO: 3)

Primer 2:
5'-CATAGGCCGAGGCGGCCGACATGT-3'     (SEQ ID NO: 4)
```

Primer 1 is the forward sequence started from position 1 of 5' end of SEQ ID NO: 1.

Primer 2 is the reverse sequence of the 3' end of SEQ ID NO: 1.

The amplification condition was a 50 µl reaction system containing 50 mmol/L KCl, 10 mmol/L Tris-Cl (pH 8.5), 1.5 mmol/L $MgCl_2$, 200 µmol/L dNTP, 10 pmol of each primer, 1 U Taq DNA polymerase (Clontech). The reaction was performed on a PE 9600 DNA amplifier with the following parameters: 94° C. 30 sec, 55° C. 30 sec, and 72° C. 2 min for 25 cycles. β-actin was used as a positive control, and a blank template, as a negative control in RT-PCR. The amplified products were purified with a QIAGEN kit, and linked with a pCR vector (Invitrogen) using a TA Cloning Kit. DNA sequencing results show that the DNA sequence of PCR products was identical to nucleotides 1–1268 bp of SEQ ID NO: 1.

EXAMPLE 4

Northern Blotting of Expression of Phosphatidic Acid Phosphatase 29.81 Gene

Total RNA was extracted by one-step method (Anal. Biochem 1987, 162, 156–159) with guanidinium isocyanate-phenol-chloroform. That is, homogenate the organize using 4 M guanidinium isocyanate-25 mM sodium citrate, 0.2 M sodium acetate (pH 4.0), add 1 volume phenol and 1/5 volume chloroform-isoamyl alcohol (49:1), centrifuge after mixing. Take out the water phase, add 0.8 volume isopropyl alcohol, then centrifuge the mixture. Wash the RNA precipitation using 70% ethanol, then dry, then dissolve it in the water. 20 µg RNA was electrophoresed on the 1.2% agarose gel containing 20 mM 3-(N-morpholino) propane sulfonic acid. (pH 7.0)—5 mM sodium acetate-imM EDTA—2.2 M formaldehyde. Then transfer it to a nitrocellulose filter. Prepare the $^{32}$P-labelled DNA probe with $\alpha$-$^{32}$P dATP by random primer method. The DNA probe used is the coding sequence (56 bp–871 bp) of phosphatidic acid phosphatase 29.81 amplified by PCR indicated in FIG. 1. The nitrocellulose filter with the transferred RNA was hybridized with the $^{32}$P-labelled DNA probe ($2\times10^6$ cpm/ml) overnight in a buffer containing 50% formamide—25 mM $KH_2PO_4$ (Ph 7.4)—5×Denhardt's solution and 200 µg/ml salmine. Then wash the filter in the 1×SSC—0.1% SDS, at 55° C., for 30 min. Then analyze and quantitative determinate using Phosphor Imager.

EXAMPLE 5

In Vitro Expression, Isolation and Purification of Recombinant Phosphatidic Acid Phosphatase 29.81

A pair of primers for specific amplification was designed based on SEQ ID NO: 1 and the encoding region in FIG. 1, the sequences are as follows:

```
                                           (Seq ID NO: 5)
Primer 3:   5'-CCCCATATGATGCGGGAGCTGGCCATTGAGATC-3'

(Seq ID NO: 6)
Primer 4:   5'-CCCGAATTCTCATACCGGGCCTTCGGTGATCCC-3'
```

These two primers contain a NdeI and EcoRI cleavage site on the 5' end respectively. Within the sites are the coding sequences of the 5' and 3' end of the desired gene. NdeI and EcoRI cleavage sites were corresponding to the selective cleavage sites on the expression vector pET-28b (+) (Novagen, Cat. No. 69865.3). PCR amplification was performed with the plasmid pBS-2933e11 containing the full-length target gene as a template. The PCR reaction was subject to a 50 µl system containing 10 pg pBS-2933e11 plasmid, 10 pmol of Primer-3 and 10 pmol of Primer-4, 1 µl of Advantage polymerase Mix (Clontech). The parameters of PCR were 94° C. 20 sec, 60° C. 30 sec, and 68° C. 2 min for 25 cycles. After digesting the amplification products and the plasmid pET-28 (+) by NdeI and EcoRI, the large fragments were recovered and ligated with T4 ligase. The ligated product was transformed into *E. coli* DH5α with the calcium chloride method. After cultured overnight on a LB plate containing a final concentration of 30 µg/ml kanamycin, positive clones were selected out using colony PCR and then sequenced. The positive clone (pET-2933e11) with the correct sequence was selected out and the recombinant plasmid thereof was transformed into BL21 (DE3) plySs (Novagen) using the calcium chloride method. In a LB liquid medium containing a final concentration of 30 µg/ml of kanamycin, the host bacteria BL21 (pET-2933e11) were cultured at 37° C. to the exponential growth phase, then IPTG were added with the final concentration of 1 mmol/L, the cells were cultured for another 5 hours, and then centrifuged to harvest the bacteria. After the bacteria were sonicated, the supernatant was collected by centrifugation. Then the purified desired protein-phosphatidic acid phosphatase 29.81 was obtained by a His.Bind Quick Cartridge (Novagen) affinity column with binding 6His-Tag. SDS-PAGE showed a single band at 29.81 kDa (FIG. 2). The band was transferred onto the PVDF membrane and the N terminal amino acid was sequenced by Edams Hydrolysis, which shows that the first 15 amino acids on N-terminus were identical to those in SEQ ID NO: 2.

EXAMPLE 6

Preparation of Antibody Against Phosphatidic Acid Phosphatase 29.81

The following specific phosphatidic acid phosphatase 29.81 polypeptide was synthesized by a polypeptide synthesizer (PE-ABI): NH2-Met-Arg-Glu-Leu-Ala-Ile-Glu-Ile-Gly-Val-Arg-Ala-Leu-Leu-Phe-COOH (SEQ ID NO: 7). The polypeptide was conjugated with hemocyanin and bovine serum albumin (BSA) respectively to form two composites (See Avrameas et al., Immunochemistry, 1969, 6: 43). 4 mg of hemocyanin-polypeptide composite was used to immunize rabbit together with Freund's complete adjuvant. The rabbit was re-immunized with the hemocyanin-polypeptide composite and Freund's incomplete adjuvent 15 days later. The titer of antibody in the rabbit sera was determined with a titration plate coated with 15 μg/ml BSA-polypeptide composite by ELISA. The total IgG was isolated from the sera of an antibody positive rabbit with Protein A-Sepharose. The polypeptide was bound to Sepharose 4B column activated by cyanogen bromide. The antibodies against the polypeptide were isolated from the total IgG by affinity chromatography. The immunoprecipitation approved that the purified antibodies could specifically bind to phosphatidic acid phosphatase 29.81.

EXAMPLE 7

Application of the Polynucleotide Fragments of Said Invention as Hybrid Probes Selection of suitable oligonucleotides from the polynucleotide of said invention as hybrid probes can be versatilly applied. The said probe could be used to determine the existence of polynucleotide of said invention or its homologous polynucleotide sequences by hybridization with genome, or cDNA library of normal or clinical tissues from varied sources. The said probes could be further used to determine whether polynucleotide of said invention or its homologous polynucleotide sequences are abnormally expressed in cells from normal or clinical tissues.

The aim of the following example is to select suitable oligonucletide fragments from the inventive polynucleotide SEQ ID NO: 1 as hybird probes to apply in membrane hybridization to determine whether there're polynucleotide of said invention or its homologous polynucleotide sequences in examined tissues, membrane hybridization methods include dot hybridization, Southern blot, Northern blot, and replica hybridization. All these methods follow nearly the same steps after the polynucleotide samples are immobilized on membranes. These same steps are: membranes with samples immobilized on are prehybridized in hybrid buffer not containing probes to block nonspecific binding sites of the samples on membranes. Then prehybrid buffer is replaced by hybrid buffer containing labeled probes and continue incubation at the appropriate temperature so probes hybridize with the target nucleotides. Free probes are washed off by a series of washing steps after the hybrid step. A high-stringency washing condition (relatively low salt concentration and high temperature) is applied in the said example to reduce the hybridization background and remain highly specific signal. Two types of probes are selected for the said example: the first type probes are oligonucleotides identical or annealed to the inventive polynucleotide SEQ ID NO: 1; the second type probes are oligonucleotides partially identical or partially annealed to the inventive polynucleotide SEQ ID NO: 1. Dot blot method is applied in the said example for immobilization of the samples on membrane. The strongest specific signal produced by hybridization between first type probes and samples is remained after relatively strict membrane washing steps.

Selection of Probes

The principles below should be followed and some things should be taken into consideration for selection of oligonucleotide fragments from the inventive polynucleotide SEQ ID NO: 1 as hybrid probes:

1. the optimal length of probes should be between eighteen and fifty nucleotides.
2. GC amount should be between 30% and 70%, since nonspecific hybridization increases when GC amount is more than 70%.
3. there should be no complementary regions within the probes themselves.
4. probes meeting to the requirements above could be initially selected for further computer-aided sequence analysis, which includes homology comparison between said initial selected probes and its sourced sequence region (SEQ ID NO: 1), other known genomic sequences and their complements. Generally, said initial selected probes should not be used when they share fifteen identical continuous base pairs, or 85% homology with non-target region.
5. whether said initial selected probes should be chose for final application relies on further experimental confirmation.

The following two probes could be selected and synthesized after the analysis above:

Probe one belongs to the first type probes, which is completely identical or annealed to the gene fragments of SEQ ID NO: 1 (41 Nt);

5'-TGCGGGAGCTGGCCATTGAGATCGGGGT-GCGAGCCCTGCTC-3' (SEQ ID NO: 8)

Probe two belongs to the second type probes which is a replaced or mutant sequence of the gene fragments of SEQ ID NO: 1, or of its complementary fragments (41 Nt):

5'-TGCGGGAGCTGGCCATTGAGCTCGGGGT-GCGAGCCCTGCTC-3' (SEQ ID NO: 9)

Any other frequently used reagents unlisted but involved in the following concrete experimental steps and their preparation methods can be found in the reference: Keller et al. DNA PROBES; Stockton Press, 1989 (USA) or a more commonly used molecular cloning experimental handbook (*Molecular Cloning*) (J. Sambrook et al., Acadimic press, 1998, $2^{nd}$ edition)

Sample Preparation

1. Extract DNA from Fresh or Frozen Tissues

Steps: 1) move the fresh or newly thawy tissue (source tissue of inventive polyucleotide) onto a ice-incubated dish containing phosphate-buffered saline (PBS). Cut the tissue into small pieces with a scissor or a operating knife. Tissue should be remained damp through the operation. 2) mince the tissue by centrifugation at 2,000 g for 10 minutes. 3) resuspend the pellet (about 10 ml/g) with cold homogenating buffer (0.25 mol/l saccharose; 25 mmol/l Tris-HCl, pH 7.5; 25 m mol/LnaCl; 25 mmol/L $MgCl_2$. 4) at 4° C., and homogenate tissue suspension at full speed with an electronic homogenizer until it's completely smashed. 5) centrifuge at 1,000 g for 10 minutes. 6) resuspend the cell pellet (1–5 ml per 0.1 g initial tissue sample), and centrifuge at 1,000 G for 10 minutes. 7) resuspend the pellet with lysis buffer (1–5 ml per 0.1 g initial tissue sample), and continue to use the phenol extraction method.

2. Phenol Extraction of DNA

Steps: 1) wash cells with 1-10 ml cold PBS buffer and centrifuge at 1000 g for 10 minutes. 2) resuspend the precipitated cells with at least 100 ul cold cell lysis buffer ($1\times10^8$ cells/ml). 3) add SDS to a final concentration of 1%. Addition of SDS into the cell precipitation before cell resuspension will cause the formation of large balls by cells which is difficult to be smashed and total production will be reduced. This phenomenon is especially severe when extracting more than $10^7$ cells. 4) add protease K to the final concentration of 200 ug/ml. 5) incubate at 50° C. for an hour or shake gently overnight at 37° C. 6) add an equal volume of phenol:chloroform:isoamyl alcohol (25:24:1) to the DNA solution to be purified in a microcentrifuge tube, and centrifuge for 10 minutes. If the two phases are not clearly separated, the solution should be recentrifuged. 7) remove the water phase to a new tube. 8) add an equal volume of chloroform: isoamyl alcohol (24:1) and centrifuge for 10 minutes. 9) remove the water phase containing DNA to a new tube and then purify DNA by ethanol precipitation.

3. DNA Purification by Ethanol Precipitation

Steps: 1) add 1/10 vol of 2 mol/L sodium acetate and 2 vol of cold 100% ethanol into the DNA solution, mix and place at −20° C. for an hour or overnight. 2) centrifuge for 10 minutes. 3) carefully spill the ethanol. 4) add 500 ul of cold 70% ethanol to wash the pellet and centrifuge for 5 minutes. 5) carefully spill the ethanol, add 500 ul cool ethanol to wash the pellets and centrifuge for 5 minutes. 6) carefully spill the ethanol and invert the tube on bibulous paper to remove remnant ethanol. Air dry for 10–15 minutes to evaporate ethanol on pellet surface. But notice not to dry the pellet completely since completely dry pellet is difficult to be dissolved again. 7) resuspend the DNA pellet with a small volume of TE or water. Spin at low speed or blow with a drip tube, and add TE gradually and mix until DNA is completely dissolved. Add about 1 µl TE every $1-5\times10^6$ cells.

The following 8–13 steps are applied only when contamination must be removed, otherwise go to step 14 directly.

8) add RNase A into DNA solution to a final concentration of 100 ug/ml and incubate at 37° C. for 30 minutes. 9) add SDS and protease K to the final concentration of 0.5% and 100 ug/ml individually, and incubate at 37° C. for 30 minutes. 10) add an equal volume of phenol:chloroform: isoamyl alcohol (25:24:1), and centrifuge for 10 minutes. 11) carefully remove out the water phase and extract it with an equal volume of chloroform: isoamyl alcohol (24:1) and centrifuge for 10 minutes. 12) carefully remove out the water phase, and add 1/10 vol of 2 mol/L sodium acetate and 2.5 vol of cold 100% ethanol, then mix and place at −20° C. for an hour. 13) wash the pellet with 70% ethanol and 100% ethanol, air dry and resuspend DNA as same as the steps 3–6. 14) determine the purity and production of DNA by $A_{260}$ and $A_{280}$ assay. 15) separate DNA sample into several portions and store at 20° C.

Preparation of Sample Membrane

1) Take 4×2 pieces of nitrocellulose membrane (NC membrane) of desired size, and lightly mark out the sample dot sites and sample number with a pencil. Every probe needs two pieces of NC membrane, so then membranes could be washed under high stringency condition and stringency condition individually in the following experimental steps.

2) Suck 15 µl of samples and control individually, dot them on the membrane, and dry at room tempreture.

3) Place the membranes on filter paper soaked in 0.1 mol/LNaOH, 1.5 mol/L NaCl, leave for 5 minutes (twice), and allow to dry. Transfer the membranes on filter paper soaked in 0.5 mol/L Tris-HCl (pH 7.0), 3 mol/L NaCl, leave for 5 minutes (twice), and allow to dry.

4) Place the membranes between clean filter paper, packet with aluminum foil, and vacuum dry at 60-80° C. for 2 hours.

Labeling of Probes

1) Add 3 ul probe (0.1 OD/10 µl), 2 ul kinase buffer, 8–10 µCi $\gamma$-$^{32}$P-dATP+2U Kinase, and add water to the final volume of 20 µl.

2) Incubate at 37° C. for 2 hours.

3) Add 1/5 vol bromophenol blue indicator (BPB).

4) Load that sample on Sephadex G-50 column.

5) Collect the first peak before the elution of $^{32}$P-Probe (monitor the eluting process by Monitor).

6) Five drops each tube and collect for 10–15 tubes.

7) Measure the isotope amount with liquid scintillator

8) Merged collection of the first peak is the prepared $^{32}$P-Probe (the second peak is free $\gamma$-$^{32}$P-dATP).

Prehybridization

Place the sample membranes in a plastic bag, add 3–10 mg prehybrid buffer (10× Denhardt s; 6×SSC, 0.1 mg/ml CT DNA (calf thymus gland DNA)), seal the bag, and shake on a 68° C. water bath for two hours.

Hybridization

Cut off a corner of the plastic bag, add in prepared probes, seal the bag, and shake on a 42° C. water bath overnight.

Membrane washing

Membrane Washing Applying a High-Stringency Condition

1) Take out the hybridized sample membranes

2) Wash the membranes with 2×SSC, 0.1% SDS at 40° C. for 15 minutes (twice).

3) Wash the membranes with 0.1×SSC, 0.1% SDS at 40° C. for 15 minutes (twice).

4) Wash the membranes with 0.1×SSC, 0.1% SDS at 55° C. for 30 minutes (twice), and dry at room temperature.

Membrane Washing Applying a Low-Stringency Condition

1) Take out the hybridized sample membranes.

2) Wash the membranes with 2×SSC, 0.1% SDS at 37° C. for 15 minutes (twice).

3) Wash the membranes with 0.1×SSC, 0.1% SDS at 37° C. for 15 minutes (twice).

4) Wash the membranes with 0.1×SSC, 0.1% SDS at 40° C. for 15 minutes (twice), and dry at room temperature.

X Ray Autoradiography

X ray autoradiograph at −70° C. (autoradiograph time varies according to radioactivity of the hybrid spots)

Experimental Results

In hybridization experiments carried out under low-stringency membrane washing condition, the radioactivity of all the above two probes hybrid spots shows no obvious difference; while in hybridization experiments carried out under high-stringency membrane washing condition, radioactivity of the hybrid spot by probe one is obviously stronger than the other three's. So probe one could be applied in qualitative and quantitive analysis of the existence and differential expression of inventive polynucleotide in different tissues.

We claim:

1. An isolated polynucleotide selected from the group consisting of:
   (a) a polynucleotide encoding a polypeptide that comprises SEQ ID NO: 2; or
   (b) a polynucleotide fully complementary to polynucleotide (a).

2. A polynucleotide of claim 1 wherein the sequence of said polynucleotide comprises position 56–871 of SEQ ID NO: 1.

3. A polynucleotide of claim 2 wherein the sequence of said polynucleotide comprises position 1–1268 of SEQ ID NO: 1.

4. A recombinant vector comprising a polynucleotide of claim 1, and a suitable regulatory element.

5. An isolated host cell comprising a polynucleotide of claim 1.

6. A method for producing a polypeptide having an activity of a phosphatidic acid phosphatase which comprises the steps of:
   (a) culturing an engineered host cell of claim 5 under conditions suitable for the expression of a phosphatidic acid phosphatase; and
   (b) isolating the polypeptide having the activity of a phosphatidic acid phosphatase from the culture.

* * * * *

```
                              SEQUENCE LISTING

<160> NUMBER OF SEQ ID NOS: 9

<210> SEQ ID NO 1
<211> LENGTH: 1268
<212> TYPE: DNA
<213> ORGANISM: Homo sapiens
<220> FEATURE:
<221> NAME/KEY: CDS
<222> LOCATION: (56)..(871)

<400> SEQUENCE: 1
ggcgggagcc gcggagagca ccagctgtcg ccgcgggagc tgctccggcc gcacc atg      58
                                                              Met
                                                                1 cgg gag ctg gcc att gag atc ggg gtg cga gcc ctg ctc ttc gga gtc     106
Arg Glu Leu Ala Ile Glu Ile Gly Val Arg Ala Leu Leu Phe Gly Val
            5                  10                  15 ttc gtt ttt aca gag ttt ttg gat ccg ttc cag aga gtc atc cag cca     154
Phe Val Phe Thr Glu Phe Leu Asp Pro Phe Gln Arg Val Ile Gln Pro
         20                  25                  30 gaa gag atc tgg ctc tat aaa aat cct ttg gtg caa tca gat aac ata     202
Glu Glu Ile Trp Leu Tyr Lys Asn Pro Leu Val Gln Ser Asp Asn Ile
     35                  40                  45 cct acc cgc ctc atg ttt gca att tct ttc ctc aca ccc ctg gct gtt     250
Pro Thr Arg Leu Met Phe Ala Ile Ser Phe Leu Thr Pro Leu Ala Val
 50                  55                  60                  65 att tgt gtg gtg aaa att atc cgg cga aca gac aag act gaa att aag     298
Ile Cys Val Val Lys Ile Ile Arg Arg Thr Asp Lys Thr Glu Ile Lys
                 70                  75                  80 gaa gcc ttc tta gcg gtg tcc ttg gct ctt gct ttg aat gga gtc tgc     346
Glu Ala Phe Leu Ala Val Ser Leu Ala Leu Ala Leu Asn Gly Val Cys
             85                  90                  95 aca aac act att aaa tta ata gtg gga aga cct cgc ccc gat ttc ttt     394
Thr Asn Thr Ile Lys Leu Ile Val Gly Arg Pro Arg Pro Asp Phe Phe
        100                 105                 110 tac cgc tgc ttt cca gat gga gtg atg aac tcg gaa atg cat tgc aca     442
Tyr Arg Cys Phe Pro Asp Gly Val Met Asn Ser Glu Met His Cys Thr
    115                 120                 125 ggt gac ccc gat ctg gtg tcc gag ggc cgc aaa agc ttc ccc agc atc     490
Gly Asp Pro Asp Leu Val Ser Glu Gly Arg Lys Ser Phe Pro Ser Ile
130                 135                 140                 145 cat tcc tcc ttt gcc ttt tcg ggc ctt ggc ttc acg acg ttc tac ttg     538
His Ser Ser Phe Ala Phe Ser Gly Leu Gly Phe Thr Thr Phe Tyr Leu
                150                 155                 160 gcg ggc aag ctg cac tgc ttc acc gag agt ggg cgg gga aag agc tgg     586
Ala Gly Lys Leu His Cys Phe Thr Glu Ser Gly Arg Gly Lys Ser Trp
            165                 170                 175 cgg ctc tgt gct gcc atc ctg ccc ttg tac tgc gcc atg atg att gcc     634
Arg Leu Cys Ala Ala Ile Leu Pro Leu Tyr Cys Ala Met Met Ile Ala
        180                 185                 190 ctg tcc cgc atg tgc gac tac aag cat cac tgg caa gat tcc ttt gtg     682
Leu Ser Arg Met Cys Asp Tyr Lys His His Trp Gln Asp Ser Phe Val
    195                 200                 205
```

-continued

| | | | | | | | | | | | | | | | |
|---|---|---|---|---|---|---|---|---|---|---|---|---|---|---|---|
| ggt | gga | gtc | atc | ggc | ctc | att | ttt | gca | tac | att | tgc | tac | aga | cag | cac | 730 |
| Gly | Gly | Val | Ile | Gly | Leu | Ile | Phe | Ala | Tyr | Ile | Cys | Tyr | Arg | Gln | His | |
| 210 | | | | 215 | | | | 220 | | | | 225 | | | | |

| tat | cct | cct | ctg | gcc | aac | aca | gct | tgc | cat | aaa | ccc | tac | gtt | agt | ctg | 778 |
| Tyr | Pro | Pro | Leu | Ala | Asn | Thr | Ala | Cys | His | Lys | Pro | Tyr | Val | Ser | Leu | |
| | | | 230 | | | | | 235 | | | | | 240 | | | |

| cga | gtc | cca | gcc | tca | ctg | aag | aaa | gag | gag | agg | ccc | aca | gct | gac | agc | 826 |
| Arg | Val | Pro | Ala | Ser | Leu | Lys | Lys | Glu | Glu | Arg | Pro | Thr | Ala | Asp | Ser | |
| | | | 245 | | | | | 250 | | | | | 255 | | | |

| gca | ccc | agc | ttg | cct | ctg | gag | ggg | atc | acc | gaa | ggc | ccg | gta | tga | | 871 |
| Ala | Pro | Ser | Leu | Pro | Leu | Glu | Gly | Ile | Thr | Glu | Gly | Pro | Val | | | |
| | | | 260 | | | | | 265 | | | | | 270 | | | | ccagtgtcct gggaggatgg acactaagcc ctgggcacat ctgccaccct gacatcataa 931
cacaatagaa atggttttct gtagtgtatt tttcatcagt tgtttctcaa agtcatcgta 991
cttctgcttc tgtttcactg atggtgttcc tgctacttta aatgtctact tccaacatcc 1051
ttgaatttgc aagtgaagga caacaatctc tgagagacgt gtggaagagg ctgtgaaggt 1111
ggggtttggg gagcttggcc gattcgtcta tctgaaatgt ttgctgtaac agccaccttc 1171
ctatgttttc atggttgtaa aacataataa aacctcccac gtggaagact tggtgttggc 1231
aaaaaaaaaa aaaacatgtc ggccgcctcg gcctatg 1268

<210> SEQ ID NO 2
<211> LENGTH: 271
<212> TYPE: PRT
<213> ORGANISM: Homo sapiens

<400> SEQUENCE: 2

Met Arg Glu Leu Ala Ile Glu Ile Gly Val Arg Ala Leu Leu Phe Gly
1               5                   10                  15

Val Phe Val Phe Thr Glu Phe Leu Asp Pro Phe Gln Arg Val Ile Gln
                20                  25                  30

Pro Glu Glu Ile Trp Leu Tyr Lys Asn Pro Leu Val Gln Ser Asp Asn
            35                  40                  45

Ile Pro Thr Arg Leu Met Phe Ala Ile Ser Phe Leu Thr Pro Leu Ala
        50                  55                  60

Val Ile Cys Val Lys Ile Ile Arg Arg Thr Asp Lys Thr Glu Ile
65                  70                  75                  80

Lys Glu Ala Phe Leu Ala Val Ser Leu Ala Leu Ala Leu Asn Gly Val
                85                  90                  95

Cys Thr Asn Thr Ile Lys Leu Ile Val Gly Arg Pro Arg Pro Asp Phe
            100                 105                 110

Phe Tyr Arg Cys Phe Pro Asp Gly Val Met Asn Ser Glu Met His Cys
        115                 120                 125

Thr Gly Asp Pro Asp Leu Val Ser Glu Gly Arg Lys Ser Phe Pro Ser
    130                 135                 140

Ile His Ser Ser Phe Ala Phe Ser Gly Leu Gly Phe Thr Thr Phe Tyr
145                 150                 155                 160

Leu Ala Gly Lys Leu His Cys Phe Thr Glu Ser Gly Arg Gly Lys Ser
                165                 170                 175

Trp Arg Leu Cys Ala Ala Ile Leu Pro Leu Tyr Cys Ala Met Met Ile
            180                 185                 190

Ala Leu Ser Arg Met Cys Asp Tyr Lys His His Trp Gln Asp Ser Phe
        195                 200                 205

Val Gly Gly Val Ile Gly Leu Ile Phe Ala Tyr Ile Cys Tyr Arg Gln

-continued

```
                    210                 215                 220
His Tyr Pro Pro Leu Ala Asn Thr Ala Cys His Lys Pro Tyr Val Ser
225                 230                 235                 240

Leu Arg Val Pro Ala Ser Leu Lys Lys Glu Glu Arg Pro Thr Ala Asp
                245                 250                 255

Ser Ala Pro Ser Leu Pro Leu Glu Gly Ile Thr Glu Gly Pro Val
                260                 265                 270

<210> SEQ ID NO 3
<211> LENGTH: 24
<212> TYPE: DNA
<213> ORGANISM: Artificial
<220> FEATURE:
<223> OTHER INFORMATION: oligonucleotide primer

<400> SEQUENCE: 3
ggcgggagcc gcggagagca ccag                                      24

<210> SEQ ID NO 4
<211> LENGTH: 24
<212> TYPE: DNA
<213> ORGANISM: Artificial
<220> FEATURE:
<223> OTHER INFORMATION: oligonucleotide primer

<400> SEQUENCE: 4
cataggccga ggcggccgac atgt                                      24

<210> SEQ ID NO 5
<211> LENGTH: 33
<212> TYPE: DNA
<213> ORGANISM: Artificial
<220> FEATURE:
<223> OTHER INFORMATION: oligonucleotide primer

<400> SEQUENCE: 5
ccccatatga tgcgggagct ggccattgag atc                            33

<210> SEQ ID NO 6
<211> LENGTH: 33
<212> TYPE: DNA
<213> ORGANISM: Artificial
<220> FEATURE:
<223> OTHER INFORMATION: oligonucleotide primer

<400> SEQUENCE: 6
cccgaattct cataccgggc cttcggtgat ccc                            33

<210> SEQ ID NO 7
<211> LENGTH: 15
<212> TYPE: PRT
<213> ORGANISM: Artificial
<220> FEATURE:
<223> OTHER INFORMATION: partial sequence of SEQ ID NO: 2

<400> SEQUENCE: 7

Met Arg Glu Leu Ala Ile Glu Ile Gly Val Arg Ala Leu Leu Phe
1               5                   10                  15

<210> SEQ ID NO 8
<211> LENGTH: 41
<212> TYPE: DNA
<213> ORGANISM: Artificial
<220> FEATURE:
<223> OTHER INFORMATION: oligonucleotide primer
```

```
<400> SEQUENCE: 8
tgcgggagct ggccattgag atcggggtgc gagccctgct c                        41

<210> SEQ ID NO 9
<211> LENGTH: 41
<212> TYPE: DNA
<213> ORGANISM: Artificial
<220> FEATURE:
<223> OTHER INFORMATION: oligonucleotide primer

<400> SEQUENCE: 9
tgcgggagct ggccattgag ctcggggtgc gagccctgct c                        41
```